United States Patent
Finke

(10) Patent No.: US 9,480,278 B2
(45) Date of Patent: Nov. 1, 2016

(54) DIET FOR ALTERING THE NUTRIENT COMPOSITION OF FEEDER INSECTS

(71) Applicant: Mark Finke LLC, Rio Verde, AZ (US)

(72) Inventor: Mark D. Finke, Rio Verde, AZ (US)

( * ) Notice: Subject to any disclaimer, the term of this patent is extended or adjusted under 35 U.S.C. 154(b) by 0 days.

(21) Appl. No.: 14/938,331

(22) Filed: Nov. 11, 2015

(65) Prior Publication Data

US 2016/0058055 A1     Mar. 3, 2016

Related U.S. Application Data

(63) Continuation of application No. 13/557,497, filed on Jul. 25, 2012, now Pat. No. 9,210,916.

(51) Int. Cl.
    *A23K 1/16*      (2006.01)
    *A23L 1/302*      (2006.01)
    *A01K 67/033*      (2006.01)

(52) U.S. Cl.
    CPC .............. *A23L 1/302* (2013.01); *A01K 67/033* (2013.01); *A23K 20/158* (2016.05); *A23K 20/174* (2016.05); *A23K 50/90* (2016.05); *A23L 33/12* (2016.08); *A23L 33/15* (2016.08); *A23L 33/155* (2016.08); *A23V 2002/00* (2013.01)

(58) Field of Classification Search
    CPC ............. A01K 67/033; A23K 1/1873; A23K 1/1603; A23K 1/1631; A23K 1/164; A23K 1/1643
    USPC ......... 426/2, 62, 92, 618, 630, 635; 119/6.7; 424/93.45
See application file for complete search history.

(56) References Cited

U.S. PATENT DOCUMENTS

| | | |
|---|---|---|
| 6,758,162 B1 | 7/2004 | Van Heygen |
| 7,174,847 B1 | 2/2007 | Hulteen, III |
| 2009/0285937 A1 | 11/2009 | Vadis et al. |

OTHER PUBLICATIONS

Allen M.E., Oftedal O.T. Dietary manipulation of the calcium content of feed crickets. Journal of Zoo and Wildlife Medicine. 1989. vol. 20, pp. 26-33.
Anderson S.J. Increasing calcium levels in cultured insects. Zoo Biology. 2000. vol. 19, pp. 1-9.
Barker D, Fitzpatrick M.P., Dierenfeld E.S. Nutrient composition of selected whole invertebrates. Zoo Biology. 1998. vol. 17, pp. 123-134.
Finke M.D., Complete nutrient composition of commercially raised invertebrates used as food for insectivores. Zoo Biology. 2002. vol. 21, pp. 286-293.
Finke M.D., Dunhame S., Kwabi C. Evaluation of four dry commercial gut loading products for improving the calcium content of crickets, Acheta domesticus. Journal of Herpetological Medicine and Surgery. 2005. vol. 15, pp. 7-12.
Klasing K.C., Thacker P. Lopez M.A. Calvert C.C. Increasing the calcium content of mealworms (Tenebrio molitor) to improve their nutritional value for bone mineralization of growing chicks. Journal of Zoo and Wildlife Medicine. 2000. vol. 31, pp. 512-517.
Oonincx D.G.A.B., Dierenfeld E. An investigation into the chemical composition of alternative invertebrate prey. Zoo Biology. 2011. vol. 29, pp. 1-15.

*Primary Examiner* — Jyoti Chawla
(74) *Attorney, Agent, or Firm* — Thomas W. Galvani, P.C.; Thomas W. Galvani

(57) ABSTRACT

A diet for altering the nutrient composition of a feeder insect includes a feed composition of feed material and nutrients. The diet is provided in a variety of forms, including as a powder or dry pellet. The nutrients in the diet include a carotenoid, essential fatty acid, and vitamin E in selected quantities and ratios.

20 Claims, No Drawings

DIET FOR ALTERING THE NUTRIENT COMPOSITION OF FEEDER INSECTS

CROSS-REFERENCE TO RELATED APPLICATIONS

This application is a continuation of and claims the benefit of pending U.S. patent application Ser. No. 13/557,497, filed Jul. 25, 2012, which is hereby incorporated by reference.

FIELD OF THE INVENTION

The present invention relates generally to feeder insects, and more particularly to altering the nutrient composition of feeder insects to provide a broad nutrient spectrum to captive insectivores that consume feeder insects.

BACKGROUND OF THE INVENTION

Insects are a primary source of nutrients and energy for a large number of animals. Wild insectivores typically feed on a wide variety of invertebrates, such as insects, spiders, isopods, ticks, millipedes, centipedes, and other arthropods. Since wild insectivores eat the food that they happen across in nature, there is high variability in the type of wild insect that becomes an insectivore's meal. Additionally, each wild insect likely differs significantly in nutrient composition from other insects the wild insectivore may consume. As such, the wild insectivore not only eats a wide variety of wild insects, but each wild insect consumed possesses a broad nutrient profile. Wild insectivores thus eat a broad, varied diet which includes a full nutrient spectrum that supports a lengthy, healthy life.

For animals kept in captivity, such as reptiles, birds, mammals, fish and invertebrates in zoos and homes, feeder insects replace wild insects as the main and most important source of food and nutrients. Feeder insects are typically purchased by the captive insectivore owner, whether a commercial establishment or a hobbyist pet owner, in bulk and often become the exclusive component of the diet of the insectivore. For example, most pet owners have only three to four different types of feeder insects available to purchase from a local pet store; crickets, mealworms, superworms, and waxworms are typically the primary feeder insects available. A pet owner may purchase all four, or, for simplicity, the pet owner may purchase only a single feeder insect type and feed that to the pet exclusively. The captive insectivore is thus exposed to a very limited diet of feeder insects.

Compounding the problems associated with the consumption of only a few types of feeder insects by a captive insectivore, the feeder insects themselves provide a very limited nutrient profile. The vast majority of feeder insects are grown by large commercial grower operations, in which feeder insects have diets designed to enhance growth rather than nutrition. While such feeder insects may be good sources of nutrients such as protein, amino acids, trace minerals, and most B-vitamins, many other important nutrients are lacking, such as vitamin E, carotenoids, essentially fatty acids, vitamin A, and other nutrients beneficial for the health of the feeder insect.

Because commercial growers grow feeder insects during a growth phase of the feeder insect life cycle and ship the feeder insects during a maintenance phase of the life cycle, commercial growers focus on developing the size and weight of the feeder insect. While insect species vary in the length of their growth phases, most commercially-grown feeder insects have a growth phase ranging between 3 days to 30 days. For instance, small crickets are grown for about 3 to about 5 days, while adult crickets have growth phases lasting for approximately 25 to approximately 30 days. Mealworms and superworms have growth phases lasting for approximately 10 to approximately 30 days. During the growth phase, the diet fed to the feeder insect is directed toward improving the raw growth of the feeder insect, rather than the nutritional quality of the feeder insect as a food source for insectivores. Following growth, during the maintenance phase of the life cycle of the feeder insects, the feeder insects are shipped to stores, where feeder insects will sit for approximately a few days to a few weeks before being purchased by a consumer. After purchase, feeder insects will generally be kept at the consumer's house for as little as 24 hours to as long as one to six weeks until being fed to an insectivore. Some feeder insects, such as mealworms, can be refrigerated to increase the life span. The feeder insects purchased by the hobbyist or zoo lack many nutrients. When the zoo or hobbyist is ready to feed the captive insectivore, in order to provide the insectivore with a complete spectrum of nutrients, the zoo or hobbyist must supplement feeder insects with nutrients before feeding the feeder insects to insectivores.

Currently, zoos and hobbyists fortify feeder insects with nutritional content in one of two ways. One method, known as "gut loading," involves forcibly feeding a diet high in a few nutrients and soon thereafter feeding the feeder insect to the insectivore. In this manner, the feeder insect's gut essentially becomes a short-term delivery capsule for retaining consumed nutrients and providing the nutrients in the feeder insect's diet directly to the insectivore.

Many of the nutrients are passed through the digestive system of the feeder insect before the feeder insect is consumed, however, so to provide nutrients to the insectivore in this manner, the feeder insect must be fed a gut-loaded diet that is extremely high in nutrients. Unfortunately, despite the fact that the gut-loading diet is fed after the growth phase and during the maintenance phase of the feeder insect, the gut-loading diet is not a maintenance diet; gut-loading diets can be toxic to feeder insects due to the high concentrations of nutrients. Gut-loaded insects typically live for only approximately 96 hours following introduction of a gut-loading diet. Immediately following introduction of the gut-loading diet, the feeder insect begins to eliminate many of the nutrients in the diet. Gut-loaded nutrients are absorbed by the gut-loaded feeder insect during the first 36 to 48 hours following introduction of the gut-loading diet, which is the approximate amount of time required for the insect to fill the entire gastrointestinal tract with the newly-consumed food. The nutrients level may plateau for a period of time or begin to decline as the feeder insect consumes less food because the feeder insect begins to lose vitality or because of the poor palatability of the diet.

In addition to the very small window of time that a gut-loaded feeder insect is useful as food, the gut-loading diet presents other problems. For instance, because feeder insects die soon after gut-loading, gut-loaded feeder insects must be separated from feeder insects being fed a maintenance diet, which can be burdensome for zoos and hobbyists. Moreover, some feeder insects will not accept gut-loaded diets at all; waxworms and large-size soldier fly larvae stop eating following the growth phase. Further, the gut and gut contents of many feeder insects are only between approximately 4% and approximately 8% by weight of the feeder insect, so the feeder insect can only carry nutrients in a very small proportion of the total body mass of the feeder insect. In crickets, the gut and gut contents are approximately 4.5% to approximately 6% of the total body weight. Further still, few hobbyists have access to raw materials or the knowledge to produce gut-loading diets, and because proper gut-loading can be very difficult to administer when using a commercially-purchased gut-loading diet, the hobbyist can inaccurately dose the feeder insect and improperly feed the insectivore. Yet still further, some nutrients depress the palatability of the feeder insect, thus reducing the likelihood that the insectivore will consume the feeder insect and the nutrients its gut contains. For these reasons and more, properly supplementing, maintaining, and using feeder insects is incredibly difficult for insectivore owners.

Another method employed by zoos and hobbyists is called "dusting." In the dusting method, nutrients are desiccated, combined, and then dusted or applied to the exterior of the feeder insects prior to feeding to the insectivore. While dusted nutrients do adhere to the exterior of some feeder insects, such as crickets, nutrients do not adhere well to the exterior of other feeder insects, such as mealworms, superworms, and waxworms. Moreover, all feeder insects groom themselves, and as such, will quickly begin to groom off any nutrients that have adhered, thus limiting the amount of time in which the nutrients are available to be fed to the insectivore. Crickets, for example, are known to dust the nutrients off within 1-2 minutes of application. Further, some nutrients are not readily amenable to being desiccated, and others have unpleasant flavors that reduce insectivore consumption. Still further, because of the difficulty in dusting all feeder insects consistently, and because of the problems associated with adherence and grooming, it is very difficult to accurately and consistently dust a feeder insect such that the feeder insect will carry an optimum level of nutrients when consumed by the insectivore.

There is very little information known about how insects process nutrients. It is not well understood how particular levels and combinations of nutrients interact in insects, are absorbed and stored, are digested and processed, or are eliminated by insects. For these problems and others, many pet insectivores suffer from a host of nutritional deficiencies.

SUMMARY OF THE INVENTION

A diet for altering the nutrient composition of a feeder insect includes a feed composition of feed material and nutrients. The nutrients include a carotenoid, an essential fatty acid, and vitamin E. The carotenoid is one of a group including beta-carotene in the range of 0.3 to 1,496.4 milligrams per kilogram of feed composition, lutein in the range of 58.7 to 2,310.8 milligrams per kilogram of feed composition, and zeaxanthin in the range of 58.7 to 2,310.8 milligrams per kilogram of feed composition. The essential fatty acid is one of a group including eicosapentaenoic acid and docosahexaeonic acid. The vitamin E includes an amount between 69 and 1,930 IU per kilogram of feed composition.

DETAILED DESCRIPTION

The invention includes a diet and method of altering the nutrient composition of a feeder insect. According to the principle of the invention, a feeder insect is fed a diet consisting of feed material in combination with nutrients during a growth phase of the feeder insect so that the tissues of the feeder insect absorb the nutrients during growth of the feeder insect. The feeder insect is then fed to an insectivore for consumption, providing a broad spectrum of nutrients to the insectivore.

The feeder insect is a food item for feeding to an insectivore. The feeder insect is one of a hemimetabolous type and a homometabolous type. Hemimetabolous insects, such as crickets and roaches, have three life stages consisting of egg, nymph, and adult. The nymph stage is a growth phase. Homometabolous insects, such as mealworms and fruit flies, have four life stages consisting of egg, larva, pupae, and adult, of which the larva stage is a growth phase. During the growth phase, the feeder insects consumes food and grows in size toward an adult. The feeder insect includes any of several types of insects, including: a) crickets, such as house crickets (*Acheta domesticus*) and field crickets (*Gryllus bimaculatus*); b) mealworms, such as the larvae of the beetle *Tenebrio molitor*; c) superworms, such as the larvae of the beetle *Zophobas mori*; d) waxworms, such as the larvae of the wax moth *Gallaria mellonella*; e) soldier fly larvae (*Hermetia illucens*); f) cockroaches, such as Turkistan Roaches (*Blatta lateralis*), Guyana Orange Spotted Roaches (*Blaptica dubia*), Lobster Roaches (*Nauphoeta cinerea*), Orange Head Roaches (*Eublaberus prosticus*), Discoid Roaches (*Blaberus discoidales*), and Madagascar Hissing Roaches (*Gromphradorhina portentosa*); g) fruit flies (*Drosophila melanogaster* and *Drosophila hydei*); h) silkworms, such as the larvae of the moth *Bombyx mori*; and i) hornworms, such as the larvae of the moth *Manduca sexta*. It should be understood that the enumeration of these particular feeder insects does not exclude other insects suitable for the purpose of the invention.

The feeder insect has a gut and tissues not including the gut, such as muscle, fat, nerves, brains, eyes, other organs and other non-gut body parts. Food consumed by the feeder insect is briefly stored in the gut and is then absorbed as nutrients and other compounds and stored in the tissues of the feeder insect for long-term storage (greater than 36 hours) or for the life of the feeder insect, which tissues make up more than 10% of the feeder insect by weight. Between approximately 92% and 96% of the feeder insect by weight includes tissues other than the gut, and the nutrients from the diet are preferably stored in the 96% of the feeder insect by weight.

According to the principle of the invention, a diet is fed to the feeder insect to alter the nutrient composition of the tissues of the feeder insect. The diet is a feed composition including nutrients and feed material, such as corn, wheat, oats, barley, wheat middlings, soybean meal, corn gluten meal, fish meal, poultry by-product meal, meat and bone meal, alfalfa meal, animals fats, vegetable oils, fish oils, added vitamins and minerals, and other feed materials. For simplicity, the term "diet" will be used for "feed composition," though for purposes of this discussion, the terms are interchangeable. The diet is typically already desiccated, so that the diet can be ground into a dry powder and mixed, employing a dry or wet grinding process such as is known in the art, though some feeder insects are fed other forms of the diet. The diet is provided in one of several forms including a dry powder, pellets, or in an extruded form. Crickets, for example, are fed the diet in a dry powder form, with a moisture content less than 12% to 14% to prevent mold growth in the diet. Water is provided to the crickets separately from the diet. As the diet is fed to mealworms, the feed material in the diet is predominantly wheat middling or wheat bran, with other ingredients which may be added to enhance the growth rate of the mealworms. While mealworms can produce water from food, to promote rapid growth of the mealworm, water is provided in the form of one of carrots, potatoes, gelatin pellets, or other higher-moisture ingredient. Fruit flies are fed the diet as a wet paste composition. Adult fruit flies lay eggs in a paste in a container, and upon hatching, fruit fly larvae can eat and burrow through the paste. Once the larvae have consumed a sufficient amount of the diet to pupate, the larvae emerge from the paste to pupate.

The diet is both a growth diet and a maintenance diet and is fed to the feeder insect during the growth phase of the feeder insect for one of at least 36 hours and 96 hours, which is a sufficient amount of time for the nutrients in the diet to be absorbed substantially into the tissues of the feeder insect as the feeder insect grows. The diet is fed to the feeder insect as one of a dry powder and a pellet. The dry powder form of the diet is inexpensive to produce and requires less energy for the feeder insect to chew and digest. The dry powder form of the diet is a dry blend of the feed material and the nutrients. Crickets are provided with a pellet form as a replacement for the dry powder form of the diet and are provided with water separately.

When the diet is fed to the feeder insect, the diet is introduced to the feeder insect for consumption. Following mastication, the diet enters the gastrointestinal system of the feeder insect. The gastrointestinal system includes the foregut, the midgut, and the hindgut. The foregut, midgut, and hindgut define the gut of the feeder insect, which, in different feeder insect species, is acidic or alkaline. The diet first enters the foregut, where it is held in preparation for passage through the gastrointestinal system. The proventriculus at the downstream end of the foregut is responsible for further reducing large food particles in the diet into smaller particles suitable for digestion. After leaving the foregut, the diet enters the midgut, which has two main functions. First, the midgut is the major site for the secretion of enzymes that begin the digestive process. Second, the majority of nutrient digestion and absorption occurs in the midgut. Nutrients absorbed in the midgut pass through the wall of the midgut into the body of the feeder insect. In many species of feeder insects, the pylorus is a valve or junction between the midgut and the hindgut. Material not absorbed in the midgut enters the hindgut, which in most feeder insects includes an ileum and a rectum. Reabsorption of water, ions, and some additional nutrients occurs in the hindgut with most of the water reabsorption taking place in the downstream end of the hindgut, the rectum. The rectum compresses matter in preparation for elimination through the anus. The rectum is very efficient at reabsorption of water, so that most terrestrial feeder insects produce relatively dry fecal pellets.

The diet is a growth and maintenance diet containing lower concentrations of nutrients than found in gut-loading diets and does not present toxicity problems to the insect. The feeder insect is thus able to feed on the diet for at least 36 to 48 hours without presenting toxicity-related health issues. The diet provides specific nutrients at specific levels to the feeder insect, as will now be discussed, to support the health of the insectivore that consumes the feeder insect. Specifically, the below experimental examples describe the inclusion in the diet of vitamin E, carotenoids and vitamin A, and fatty acids. The below experimental examples employed crickets as test subjects, but one having skill in the art will readily appreciate the findings are applicable to all species of feeder insects.

Vitamin E

Captive insectivores fed with current methods have been shown in past studies to be deficient in vitamin E. Feeder insects which contain between approximately 50 and approximately 200 International Units ("IU") of vitamin E per kilogram dry matter provide health benefits to captive insectivores. All references in this disclosure to concentrations in feeder insects will be based on dry matter measurements, unless otherwise specified. Experiments were performed to determine the levels of vitamin E in a feeder insect diet that would produce in the feeder insect the targeted levels between 50 and 200 IU of vitamin E per kilogram dry matter for consumption by an insectivore. In the experiments, feeder insects were fasted for 24 to 36 hours prior to analysis to ensure that food in the gut was eliminated completely so as not to affect the results. The feeder insects were provided the diet containing varying levels of vitamin E. Vitamin E analysis was then performed using the method as described by Cort, et. al., *Vitamin E Content of Feedstuffs Determined by High-Performance Liquid Chromatography Fluorescence*, JOURNAL OF AGRICULTURAL AND FOOD CHEMISTRY, Vol. 31, 1330-1333 (1983). The results in Table A below demonstrate the level of vitamin E in the diet of the feeder insect and the resultant level of vitamin E in feeder insects grown to approximately two-thirds of adult-size within approximately 21 days following introduction of the diet.

TABLE A

| Vitamin E in Diet | Vitamin E in Feeder Insect |
|---|---|
| 31 IU/kg | 38.7 IU/kg dry matter |
| 210 IU/kg | 89.2 IU/kg dry matter |
| 360 IU/kg | 117.7 IU/kg dry matter |

There is a direct relationship between the vitamin E content in the diet and the vitamin E content in the feeder insect. Since the feeder insects were fasted prior to analysis, and the results were collected when the feeder insects were grown to approximately two-thirds of adult-size within approximately 21 days after introduction of the diet, the vitamin E content in the feeder insect is a result of a change in the composition of the tissues of the feeder insect, rather than the consequence of food in the gut of the feeder insect. Regression analysis was performed on the data to establish a best-fit line defined by an equation $FI=0.241*D+33.5$, where FI is the vitamin E content of feeder insect and D is the vitamin E content in the feeder insect diet. According to the present inventive method, with this established equation, a diet, fed to the feeder insect, having a vitamin E content of between approximately 69 and approximately 691 IU per kilogram produces the targeted 50 to 200 IU of vitamin E per kilogram dry matter in the feeder insect, respectively. A similar experiment performed with mealworms showed that, when mealworms were fed a diet containing added vitamin E, those mealworms contained more vitamin E than mealworms fed a control diet.

The vitamin E requirement of wild insectivores varies with the amount and type of fat in the diet of the wild insectivore, and wild insects on which insectivores feed have vitamin E contents typically ranging between approximately 150 and approximately 500 IU per kilogram dry matter. With the regression equation $FI=0.241*D+33.5$, a feeder insect diet having a vitamin E content of between approximately 480 and approximately 1,930 IU per kilogram produces the approximately 150 to approximately 500 IU per kilogram dry matter levels found in wild insects on which wild insectivores feed.

Carotenoids

Carotenoids are not necessary for the life of an insectivore, but do support the health of an insectivore. Carotenoids are a precursor to vitamin A, enhance immune function, and provide the compounds for some of the natural colors displayed by insectivores, which can improve the aesthetic appeal of the insectivore and aid in reproduction. Commercial growers do not fortify the diets provided to feeder insects, so only low levels of carotenoids, may be present in feeder insects, mostly due to commercial diets containing lutein from corn or corn gluten meal in the feed material of the commercial diet. Furthermore, although attempts to increase the carotenoid intake of captive insectivores by gut loading feeder insects have been made, such feeder insects quickly eliminate gut-loaded carotenoids. As such, commercially-grown and purchased feeder insects typically contain little to no carotenoids.

Wild insects vary widely in carotenoid content. The range may be indicative of the wide range of foods consumed in the wild. Wild insects have been caught that possess total carotenoid levels of between 500 micrograms per kilogram dry matter of body mass and 670,000 micrograms per kilogram dry matter of body mass. An experiment was performed to determine the levels of total carotenoids in a feeder insect diet that would produce targeted levels of total carotenoids in the feeder insect within the range of 500 micrograms per kilogram dry matter of body mass to 670,000 micrograms per kilogram dry matter of body mass. By introducing sufficient carotenoids, in specific combinations, to the feeder insect so as to increase the total carotenoid content of the feeder insect to a level commensurate with that found in wild insects, the captive insectivore feeding upon the feeder insect is provided with a similar carotenoid content and associated health benefits.

In the experiment, feeder insects were fasted for 24 to 36 hours to ensure that food in the gut was eliminated completely so as not to affect the results. In the experiment, the feeder insects were fed diets containing low and high levels of added carotenoids in the form of beta-carotene, lutein, and zeaxanthin. Low levels of added carotenoids were approximately 155 milligrams per kilogram of the diet, and high levels of added carotenoids were approximately 564 milligrams per kilogram of the diet. The feeder insects were also provided with low and high levels of vitamin A, which contained approximately 12,000 and approximately 100,000 IU of vitamin A per kilogram of the diet, respectively, in the form of vitamin A palmitate. A control group of feeder insects was fed a control diet containing no additional carotenoids. Carotenoid analysis of the feeder insects was then performed on the feeder insects after feeding the diet to the feeder insects for approximately 21 days using the methods of McGraw, et. al., *Carotenoid Accumulation in the Tissues of Zebra Finches: Predictors of Integumentary Pigmentation and Implications for Carotenoid Allocation Strategies*, PHYSIOLOGICAL AND BIOCHEMICAL ZOOLOGY, Vol. 83, 97-10 (2010), and retinol and retinal analysis was performed using the methods of Von Lintig, et. al., *Filling the Gap in Vitamin A Research Molecular Identification of an Enzyme Cleaving Beta-Carotene to Retinal*, JOURNAL OF BIOLOGICAL CHEMISTRY, Vol, 275, 11915-11920 (1990). The results in Table B below demonstrate the levels of carotenoids, retinol, and retinal in the feeder insects.

TABLE B

| Nutrient in Feeder Insect | Control Diet | Diet with 155 mg/kg Carotenoids | Diet with 564 mg/kg Carotenoids | Diet with Added Vitamin A |
|---|---|---|---|---|
| Beta-carotene (μg/kg dry matter) | 33 | 2,716 | 3,233 | 33 |

TABLE B-continued

| Nutrient in Feeder Insect | Control Diet | Diet with 155 mg/kg Carotenoids | Diet with 564 mg/kg Carotenoids | Diet with Added Vitamin A |
|---|---|---|---|---|
| Zexanthin (μg/kg dry matter) | 83 | 1,233 | 16,733 | 33 |
| Lutein (μg/kg dry matter) | 333 | 800 | 11,300 | 33 |
| Retinol (μg/kg dry matter) | 6.23 | 6.93 | 9.27 | 6.00 |
| Retinal (μg/kg dry matter) | 14.20 | 23.83 | 27.90 | 15.67 |
| Total Vitamin A Activity (IU/kg dry matter) | 330 | 4,949 | 5,895 | 349 |

In this experiment, feeder insects accumulated significant amounts of all three carotenoids, beta-carotene, lutein and zeaxanthin, when beta-carotene, lutein, and zeaxanthin were added to the diet. The data exhibit a direct relationship between the total carotenoid content in the diet of the feeder insects and the total carotenoid content in the feeder insects. Feeder insects fed the diet containing 155 milligrams per kilogram exhibited total carotenoid levels of 4,750 micrograms per kilogram dry matter, and feeder insects fed the diet containing 564 milligrams per kilogram exhibited total carotenoid levels of 31,267 micrograms per kilogram dry matter, each of which values are within the 500 to 670,000 micrograms per kilogram dry matter range of total carotenoids in wild feeder insects.

The level of retinol and retinal in the feeder insect, known as the retinoid content, was also affected by the addition of carotenoids in the diet. Feeder insects fed the diet containing 155 milligrams per kilogram exhibited a retinoid content approximately 51% higher than that in the feeder insects fed the control diet, and feeder insects fed the diet containing 564 milligrams per kilogram exhibited a retinoid content approximately 82% higher than that in the feeder insects fed the control diet. In crickets, beta-carotene is a precursor for the synthesis of retinal, which crickets use as a chromophore. This is why feeder insects that fed diets containing higher levels of beta-carotene produce higher levels of retinoids. Lutein and zeaxanthin are not precursors for retinal in crickets. In other species, both lutein and zeaxanthin are precursors for 3-hydroxy retinal, which those species of insects use as a chromophore. Feeder insects such as crickets, mealworms, superworms, and cockroaches use retinal as a chromophore, while waxworms, soldier fly larvae, fruit flies, and silkworms use 3-hydroxy retinal as a chromophore.

The total vitamin A activity of the feeder insects was calculated by using the retinoid content and the beta-carotene content. The data was converted into International Units using known conversion factors, according to National Research Council, NUTRIENT REQUIREMENTS OF LABORATORY ANIMALS, 4th ed. (1995). Feeder insects fed diets containing low and high levels of carotenoids contained approximately 15 to approximately 18 times, respectively, the total vitamin A activity as those feeder insects fed the control diet, and approximately 14 to approximately 17 times, respectively, the total vitamin A activity as those feeder insects fed the diet containing added vitamin A through retinol supplementation.

Further, while it is known that carotenoids and vitamin A support the health and immune system of an insectivore such as a reptile, it is not known what minimum levels are necessary to do so. However, requisite vitamin A levels are known for rats and poultry, and it is known that avian insectivores and fish both readily utilize carotenoids as a source of vitamin A. Feeder insects fed on the control diet and the fortified vitamin A diet contained only 14% and 15%, respectively, of the required level for a rat and only 22% and 23%, respectively, of the required level for poultry. However, feeder insects fed on the diets containing low and high levels of carotenoids contain 215% and 256%, respectively, of the requirement for the rat and 330% and 393%, respectively, of the requirement for poultry. Because the vitamin A contained in a feeder insect fed according to the principle of the invention is highly available to a consuming insectivore, the feeder insect serves as a good source of vitamin A for the insectivore.

Based on other animal studies performed with chickens, turkeys, rats, mice, hamsters, dogs, cats, pigs, salmon, catfish, carp and trout, it is expected that insectivores require between 50% and 1000% of the vitamin A requirement of poultry and rats. Poultry require 1,500 IU of vitamin A per kilogram, and rats require 2,300 IU of vitamin A per kilogram. An experiment was performed to determine the levels of beta-carotene in a feeder insect diet that would produce beta-carotene levels in a feeder insect that would lead to production of vitamin A in the targeted 50% to 1000% range of the poultry and rat's requirement. The experiment produced the data presented in Table C below.

TABLE C

| Beta-carotene in Diet | Beta-carotene in Feeder Insect |
|---|---|
| 0.2 mg/kg | 33.3 µg/kg dry matter |
| 0.3 mg/kg | 33.3 µg/kg dry matter |
| 11.7 mg/kg | 2,716.7 µg/kg dry matter |
| 15.3 mg/kg | 3,233.3 µg/kg dry matter |

Regression analysis was performed on the data to establish a best-fit line defined by an equation $FI=219.2 \times D-2.92$, where FI is the beta-carotene content of feeder insect and D is the beta-carotene content in the feeder insect diet. Using the regression equation, 3 milligrams of beta-carotene per kilogram of feeder insect diet produces 655 micrograms of beta-carotene per kilogram dry matter of feeder insect, which yields 1,173 IU of vitamin A per kilogram dry matter, or approximately 51% of the rat's vitamin A requirement and approximately 78% of poultry's vitamin A requirement. Further, using the regression equation, 65 milligrams of beta-carotene per kilogram of feeder insect diet produces 14,254 micrograms of beta-carotene per kilogram dry matter of feeder insect, which yields 23,000 IU of vitamin A per kilogram dry matter, or approximately 1000% of the rat's vitamin A requirement and approximately 1600% of poultry's vitamin A requirement.

Wild insects have been caught that possess beta-carotene levels up to 328,000 micrograms per kilogram dry matter of body mass, with most wild insects containing between 15,000 and 80,000 micrograms per kilogram dry matter of body mass. Using the regression equation calculated from the data of Table C, feeder insect diets that contain between approximately 0.3 and approximately 1,496.4 milligrams of beta-carotene per kilogram yield a feeder insect containing between 62.8 and 328,000 micrograms of beta-carotene per kilogram dry matter of feeder insect. Feeder insect diets that contain between approximately 68.4 and approximately 365 milligrams of beta-carotene per kilogram yield a feeder insect containing between 15,000 and 80,000 micrograms of beta-carotene per kilogram dry matter of feeder insect.

Wild insects have been caught that possess combined lutein and zeaxanthin levels between 500 and 500,000 micrograms per kilogram dry matter of body mass, with most wild insects containing between 50,000 and 250,000 combined micrograms of lutein and zeaxanthin per kilogram dry matter of body mass. An experiment was performed to determine the levels of lutein and zeaxanthin in a feeder insect diet that would produce lutein and zeaxanthin levels in a feeder insect similar to those found in the wild. The experiment produced the data presented in Tables D and E below.

TABLE D

| Lutein in Diet | Lutein in Feeder Insect |
|---|---|
| 11.6 mg/kg | 33 µg/kg dry matter |
| 13.3 mg/kg | 333 µg/kg dry matter |
| 64.9 mg/kg | 800 µ5/kg dry matter |
| 193.6 mg/kg | 11,300 µg/kg dry matter |

TABLE E

| Zeaxanthin in Diet | Zeaxanthin in Feeder Insect |
|---|---|
| 2.9 mg/kg | 33.3 µg/kg dry matter |
| 3.2 mg/kg | 83.3 µg/kg dry matter |
| 78.8 mg/kg | 1,233.3 µg/kg dry matter |
| 355.3 mg/kg | 16,733.3 µg/kg dry matter |

Regression analysis was performed on the data to establish a best-fit line defined by an equation $FI=0.094 \times D^2 - 0.9477 \times D + 232$, where FI is the combined lutein and zeaxanthin content of feeder insect and D is the combined lutein and zeaxanthin content in the feeder insect diet. Using this regression equation, feeder insect diets that contain between approximately 58.7 and approximately 2,310.8 milligrams of lutein and zeaxanthin, in combination, per kilogram yield a feeder insect that contains between 500 and 500,000 of lutein and zeaxanthin, in combination, per kilogram dry matter of feeder insect. Feeder insect diets that contain between approximately 732.7 and approximately 1,635.1 milligrams of lutein and zeaxanthin, in combination, per kilogram yield a feeder insect that contains between 50,000 micrograms of lutein and 250,000 zeaxanthin, in combination, per kilogram dry matter of feeder insect.

Fatty Acids

The ratio of omega-6 ("n-6") to omega 3 ("n-3") fatty acids is known to play a critical role in a variety of health-related issues in animals including immune response, cancer, and many others. A low n-6/n-3 ratio, preferably less than 10:1, is beneficial. In humans, high n-6/n-3 ratios are the result of a shift to diets based on high levels of grains (such as corn, wheat, oats, rice and barley) grain by-products, and products from animals fed diets including such grains, by-products, and products. Published research on the fatty acid content of feeder insects shows most feeder insects contain high n-6/n-3 ratios, ranging from 14:1 to 38:1. Another study has shown that 66% of wild insects possess n-6/n-3 ratios of less than 10:1 while only 34% had n-6/n-3 ratios of greater than or equal to 10:1. Many aquatic feeder insects have n-6/n-3 ratios less than 1:1, due to containing up to 30% eicosapentaenoic acid ("EPA") and docosahexaenoic ("DHA").

Wild insectivores typically consume diets which contain n-6/n-3 ratios much less than that fed to commercial insectivores. While little is known concerning the effects of specific fatty acids on the health and well-being of insectivores, it is known that wild insects contain a variety of fatty acids, and wild insects which spend at least some time in an aquatic environment are especially good sources of both EPA and DHA. Wild insectivores consume foods which contain both EPA and DHA, which are omega-3 fatty acids and lead to low n-6/n-3 ratios.

Experiments were first performed to determine the current levels of fatty acids in feeder insects supplied by three different commercial growers, identified as Suppliers A, B, and C in Table F below. In the experiment, crickets were used for the feeder insects and were fasted for 24 to 36 hours to ensure that food in the gut was eliminated completely so as not to affect the results. The experiments determined the levels of linoleic acid ("LA"), alpha-linoleic acid ("ALA"), EPA, and DHA present in the feeder insects supplied by those commercial growers, according to method 996.06 from the AOAC. See AOAC International, *Method* 996.06, OFFICIAL METHODS OF ANALYSIS OF AOAC INT'L, 18$^{th}$ ed. (2005). The results are presented below in Table F, with percentages by weight listed.

TABLE F

| Nutrient | Supplier A Feeder Insects | Supplier B Feeder Insects | Supplier C Feeder Insects |
| --- | --- | --- | --- |
| LA (n-6) | 3.05% | 2.99% | 3.08% |
| ALA (n-3) | 0.14% | 0.12% | 0.12% |
| EPA (n-3) | 0.03% | Not Detected | 0.01% |
| DHA (n-3) | Not Detected | Not Detected | Not Detected |
| Total n-6 fatty acids | 3.05% | 2.99% | 3.08% |
| Total n-3 fatty acids | 0.17% | 0.12% | 0.13% |
| n-6/n-3 ratio | 18 | 25 | 24 |

The experiments demonstrated relatively high levels of omega-6 fatty acids and very low or nonexistent levels of omega-3 fatty acids in the feeder insects grown by all three commercial growers. The data also suggests little variation among the fatty acid composition of the feeder crickets grown by the three commercial growers. The ratio of omega-6 to omega-3 fatty acids were well above 10:1 in all of the feeder insects.

An experiment was next performed to determine the levels of fatty acids in a feeder insect diet that would produce targeted levels of fatty acids, similar to levels found in wild insects, in the feeder insect for consumption by the insectivore, and also that would produce a targeted ratio of omega-6 and omega-3 fatty acids below 10:1. Feeder insects in the experiment were fed one of four diets. A first diet included the commercially-available Timberline Cricket Power Food™. The first diet, which defines a control diet, contained 0.22% ALA by weight, 0.04% EPA by weight, and 0.04% DHA by weight. A second diet added 2% canola oil to the first diet and contained LA (18:2 n-6) and ALA (18:3 n-3). The second diet contained 0.37% ALA by weight, 0.05% EPA by weight, and 0.04% DHA by weight. A third diet added 2% flaxseed oil to the first diet and contained ALA (18:3 n-3). The third diet contained 1.03% ALA by weight, 0.04% EPA by weight, and 0.04% DHA by weight. A fourth diet added 2% fish oil to the first diet and contained EPA (20:5 n-3) and DHA (22:5 n-3). The fourth diet contained 0.21% ALA by weight, 0.69% EPA by weight, and 0.30% DHA by weight. The feeder insects were fed respective diets exclusively from a time period extending from hatching through to three-quarters of the growth cycle of the feeder insects, or approximately 21 days. The fatty acid contents of the feeder insects fed on the diets were then determined, which results are shown in Table G below, with percentages by weight listed.

TABLE G

| Nutrient | Control Diet | Diet with Canloa Oil | Diet with Flaxseed Oil | Diet with Fish Oil |
| --- | --- | --- | --- | --- |
| LA (n-6) | 2.81% | 2.42% | 2.58% | 2.32% |
| ALA (n-3) | 0.08% | 0.12% | 0.43% | 0.08% |
| EPA (n-3) | 0.02% | 0.02% | 0.03% | 0.11% |
| DHA (n-3) | Not Detected | Not Detected | Not Detected | 0.01% |
| Total n-6 fatty acids | 2.82% | 2.45% | 2.58% | 2.32% |
| Total n-3 fatty acids | 0.10% | 0.14% | 0.46% | 0.20% |
| n-6/n-3 ratio | 29 | 17 | 6 | 12 |

The control diet produced feeder crickets containing fatty acid compositions and an n-6/n-3 ratio consistent with the feeder insects at issue in Table F. In contrast, the second, third, and fourth diets, containing 2% canola oil, 2% flaxseed oil, and 2% fish oil, respectively, produced crickets having lower LA levels and higher omega-3 levels, contributing to lowered n-6/n-3 ratios when compared with the control diet. The relationship between the n-6/n-3 ratio in the diets and the n-6/n-3 ratio in the feeder insects fed the diets is not exactly linear because feeder insects absorb different fatty acids differently, and some feeder insects metabolize fatty acids at one rate while other feeder insects store fatty acids at another rate.

The present invention is described above with reference to a preferred embodiment. However, those skilled in the art will recognize that changes and modifications may be made in the described embodiment without departing from the nature and scope of the present invention. Various further changes and modifications to the embodiment herein chosen for purposes of illustration will readily occur to those skilled in the art. To the extent that such modifications and variations do not depart from the spirit of the invention, they are intended to be included within the scope thereof.

Having fully described the invention in such clear and concise terms as to enable those skilled in the art to understand and practice the same, the invention claimed is:

Having fully described the invention in such clear and concise terms as to enable those skilled in the art to understand and procatice the same, the invention claimed is:

1. A diet for altering the nutrient composition of a feeder insect, the diet comprising:
   a feed composition comprising feed material and nutrients, the nutrients comprising a carotenoid, an essential fatty acid, and vitamin E;
   wherein:
      the carotenoid is selected from the group consisting of beta-carotene in the range of 0.3 to 1,496.4 milligrams per kilogram of feed composition, lutein in the range of 58.7 to 2,310.8 milligrams per kilogram of feed composition, and zeaxanthin in the range of 58.7 to 2,310.8 milligrams per kilogram of feed composition;

the essential fatty acid is selected from the group consisting of eicosapentaenoic acid and docosahexaeonic acid; and the vitamin E is in the range of 69 to 1,930 IU per kilogram of feed composition.

2. The diet of claim 1, wherein the carotenoid is in the range of 155 to 1,496.4 milligrams per kilogram of feed composition.

3. The diet of claim 1, wherein the carotenoid is in the range of 155 to 564 milligrams per kilogram of feed composition.

4. The diet of claim 1, wherein the nutrients further comprise vitamin A.

5. The diet of claim 1, wherein the beta-carotene is in the range of 12,000 to 100,000 IU per kilogram of feed composition.

6. The diet of claim 1, wherein the beta-carotene is in the range of 3 to 65 milligrams per kilogram of feed composition.

7. The diet of claim 1, wherein the beta-carotene is in the range of 68.4 to 365 milligrams per kilogram of feed composition.

8. The diet of claim 1, wherein the nutrients include between 732.7 and 1,635.1 milligrams of lutein and zeaxanthin, in combination, per kilogram of feed composition.

9. The diet of claim 1, wherein the nutrients include between 0.21% and 1.03% by weight alpha-linoleic acid.

10. The diet of claim 1, wherein the nutrients include between 0.04% and 0.69% by weight eicosapentaenoic acid.

11. The diet of claim 1, wherein the nutrients include between 0.04% and 0.3% by weight docosahexaeonic acid.

12. The diet of claim 1, wherein the nutrients include omega-6 fatty acids and omega-3 fatty acids.

13. The diet of claim 1, wherein the nutrients include omega-6 fatty acids and omega-3 fatty acids in a ratio that is less than 10:1, respectively.

14. The diet of claim 1, wherein the diet has a dry powder form.

15. The diet of claim 1, wherein the diet has a pellet form.

16. A diet comprising:
a feed composition including, in combination, a carotenoid, an essential fatty acid, and vitamin E;
wherein:
the carotenoid is selected from the group consisting of beta-carotene in the range of 0.3 to 1,496.4 milligrams per kilogram of feed composition, lutein in the range of 58.7 to 2,310.8 milligrams per kilogram of feed composition, and zeaxanthin in the range of 58.7 to 2,310.8 milligrams per kilogram of feed composition;

the essential fatty acid is selected from the group consisting of eicosapentaenoic acid and docosahexaeonic acid; and the vitamin E is in the range of 69 to 1,930 IU per kilogram of feed composition.

17. The diet of claim 16, wherein the feed composition further comprises vitamin A.

18. The diet of claim 16, wherein the feed composition further comprises between 12,000 and 100,000 IU of vitamin A per kilogram of feed composition.

19. The diet of claim 16, wherein the beta-carotene is in the range of 3 to 65 milligrams per kilogram of feed composition.

20. The diet of claim 16, wherein the beta-carotene is in the range of 68.4 and 365 milligrams per kilogram of feed composition.

* * * * *